(12) United States Patent
Nair et al.

(10) Patent No.: US 9,034,930 B2
(45) Date of Patent: May 19, 2015

(54) BIODEGRADABLE POLYMERIC HYDROGEL COMPOSITION

(75) Inventors: Hemant Ravindran Nair, Maharashtra (IN); Mohan Gopalkrishna Kulkarni, Maharashtra (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/608,742

(22) Filed: Sep. 10, 2012

(65) Prior Publication Data

US 2013/0059925 A1    Mar. 7, 2013

Related U.S. Application Data

(63) Continuation of application No. PCT/IN2011/000155, filed on Mar. 9, 2011.

(30) Foreign Application Priority Data

Mar. 9, 2010   (IN) .......................................... 534/10

(51) Int. Cl.
| | | |
|---|---|---|
| *A61K 47/32* | (2006.01) | |
| *A61K 47/00* | (2006.01) | |
| *C08G 65/332* | (2006.01) | |
| *C08G 65/333* | (2006.01) | |
| *C08L 71/02* | (2006.01) | |
| *A61K 47/34* | (2006.01) | |
| *A61L 31/14* | (2006.01) | |
| *A61L 15/64* | (2006.01) | |
| *A61K 31/785* | (2006.01) | |
| *A61L 31/10* | (2006.01) | |
| *A61L 27/18* | (2006.01) | |
| *A61L 27/52* | (2006.01) | |
| *A61L 27/58* | (2006.01) | |

(52) U.S. Cl.
CPC .............. *A61K 47/34* (2013.01); *A61L 31/145* (2013.01); *A61L 15/64* (2013.01); *A61K 31/785* (2013.01); *C08L 2312/00* (2013.01); *A61L 31/10* (2013.01); *A61L 27/18* (2013.01); *A61L 27/52* (2013.01); *A61L 27/58* (2013.01); *C08G 65/3322* (2013.01); *C08G 65/33303* (2013.01); *C08G 65/33306* (2013.01); *C08G 2650/50* (2013.01); *C08L 71/02* (2013.01); *C08L 2205/02* (2013.01)

(58) Field of Classification Search
CPC ..... C08L 71/02; C08L 2205/02; A61L 27/52; A61K 47/34
See application file for complete search history.

(56) References Cited

U.S. PATENT DOCUMENTS

| | | | |
|---|---|---|---|
| 5,078,744 A | 1/1992 | Chvapil | |
| 5,998,491 A * | 12/1999 | Haar, Jr. ......................... | 521/64 |
| 6,133,297 A * | 10/2000 | Coburn et al. ................ | 514/352 |
| 6,998,115 B2 | 2/2006 | Langer et al. | |
| 2006/0210602 A1 | 9/2006 | Sehl et al. | |
| 2007/0299464 A1* | 12/2007 | Cruise et al. .................. | 606/192 |
| 2008/0253987 A1 | 10/2008 | Rehor et al. | |
| 2008/0293827 A1* | 11/2008 | Lee et al. .................... | 514/772.3 |
| 2009/0047256 A1* | 2/2009 | Bettinger et al. ............. | 424/93.7 |
| 2009/0324721 A1 | 12/2009 | Kennedy et al. | |

FOREIGN PATENT DOCUMENTS

| | | |
|---|---|---|
| WO | 2004106411 A2 | 12/2004 |
| WO | 2006109945 A1 | 10/2006 |
| WO | 2008011561 A2 | 1/2008 |
| WO | 2009042825 A2 | 4/2009 |

OTHER PUBLICATIONS

Mohan et al (Polyampholytic hydrogels . . . , online on Dec. 11, 2006, Reactive and Functional Polymers, vol. 67, pp. 144-155).*
Huynh et al. (Functionalized injectable hydrogels for controlled insulin delivery, Jun. 2008, Biomaterials, vol. 29, pp. 2527-2534).*
Ahmed (Hydrogel: Preparation, characterization and applications, Journal of Advanced Research, 2013, pp. 1-17).*
Tillet et al. (Progress in Polymer Science, 2011, vol. 36, pp. 191-217).*
Nguyen et al (Macromolecular Bioscience, 2010, vol. 10, pp. 563-579).*
Li et al. (Chem Soc Rev, 2012, vol. 41, pp. 2193-2221).*
International Search Report and Written Opinion of the International Searching Authority Application No. PCT/IN2011/000155 Completed: Jan. 12, 2012; Mailing Date: Apr. 12, 2012 14 pages.

* cited by examiner

*Primary Examiner* — Brian-Yong Kwon
*Assistant Examiner* — Mark V Stevens
(74) *Attorney, Agent, or Firm* — St. Onge Steward Johnston & Reens LLC (57) ABSTRACT

A biodegradable polymeric hydrogel composition including a component A and component B forming a β-aminoester linkage such that the linkage results in gelation, wherein component A is water soluble polymer containing acrylate functionality and component B is a water soluble amine functionality useful for medical applications such as such as drug delivery, tissue engineering, and biomaterials and method of preparation thereof.

19 Claims, 1 Drawing Sheet

BIODEGRADABLE POLYMERIC HYDROGEL COMPOSITION

CROSS-REFERENCE TO RELATED APPLICATIONS

The present application is a continuation of pending International patent application PCT/IN2011/000155 filed on Mar. 9, 2011 which designates the United States and claims priority from Indian patent application 534/DEL/2010 filed on Mar. 9, 2010. The content of all prior applications is incorporated herein by reference.

FIELD OF THE INVENTION

The present invention relates to a fast curing biodegradable polymeric hydrogel composition comprising a component A and component B forming a β-aminoester linkage such that the linkage results in gelation even at temperatures close to human body temperatures wherein component A is water soluble polymer containing acrylate functionality and component B is a water soluble amine functionality.

The present invention further relates to biodegradable polymeric hydrogel composition useful as biomaterials for medical applications such as drug delivery and tissue engineering.

BACKGROUND OF THE INVENTION

Over the last decade, biodegradable networks that can be formed in situ have been extensively researched. The advantages of using such networks compared to the conventional methods are localized delivery of active ingredient, cost effectiveness and patient compliance. Microspheres have been the choice for the delivery of drugs and proteins for long time. The major limitations of microspheres are reproducibility and the possibility of microsphere migration from the site of injection. The other disadvantage of microspheres is the number of steps involved and the need for use of solvents during synthesis of microspheres. The residual solvent is clearly undesirable during end application. Micelles have also been used in injectable drug delivery systems. However, along with the disadvantages of migration from the site of injection, the stability of micelles has been a concern. The stability of micelles depends on several variables such as critical micelle concentration, temperature, salt concentration and chemical structure of polymer. Any change in each of these variables can destabilize the micelle. In comparison to microspheres and micelles, the problem of migration of the delivery system can be eliminated by the use of an in situ formed hydrogel. The use of in situ formed hydrogel eliminates the washing and precipitation steps involved in the preparation and purification of microspheres, which can reduce the time and cost of making the product. The other distinctive advantage of in situ formed hydrogels compared to implants is the less invasive and painful insertion into the desired site. In comparison to drug delivery depot implants, the injectable hydrogels avoid the need for local anesthesia, surgical steps during implantation, post surgical complication and scars. The biodegradable hydrogels formed in situ have found application from tissue engineering (K. T. Nguyen, J. L. West, Biomaterials 23, 2002, 4307-4314) to cell release (T. Chen, D. A. Small, M. K. McDermott, W. E. Bentley, G. F. Payne, Biomacromolecules 4, 2003, 1558) and drug delivery system (A. Hatefi, B. Amsden, Journal of Controlled Release 80, 2002, 9-28).

Several methods are reported in the literature for the preparation of in situ crosslinked hydrogels, which can be broadly classified into two categories: 1. Physical crosslinking methods and 2. Chemical crosslinking methods. Physical crosslinking of hydrogels includes mechanisms such as ionic interaction, hydrophobic interaction and stereocomplexation. Ionic interaction has been used to prepare hydrogels by complexing cationic salt or polymer with anionic salt or polymer. Alginates are known to crosslink upon interaction with the ion such as calcium ion (C. P. Reis, A. J. Ribero, R. J. Neufeld, F. Veiga, Biotechnology and bioengineering, 96, 2007, 977-989). Wang et al (C. Wang, H. Liu, Q. GAO, X. Liu, Z. Tong, Carbohydrate Polymers 71, 2008, 476-480) have reported novel alginate/$CaCO_3$ hybrid hydrogels fabricated by in situ release of calcium ion by hydrolysis of D-glucano-δ-lactone to reduce pH. By controlling the alginate to $CaCO_3$ weight ratio, it was possible to tailor the mechanical strength of the hybrid hydrogels.

Amongst the physical crosslinking methods, the gels formed as a result of hydrophobic interactions have been extensively studied. The formation of the gel is a temperature dependent phenomenon. As the temperature is increased, hydrophobic association takes place which eventually leads to the formation of the gel from the sol. Research in this area has been focused on poly(ethylene glycol) or pluronic block with hydrophobic polylactide, PLGA or PTMC (S. Y. Kim, H. J. Kim, K. E. Lee, S. S. Han, Y. S. Sohn, B. Jeong, Macromolecules, 2007, 40 5519-5525; B. Jeong, Y. H. Bae, S. W. Kim Journal of Biomedical Materials Research 50, 2000, 171-177, Q. Hou, D. Y. S. Chau, C Pratoomsoot, P. J. Tighe, H. S. Dua, K. M. Shakesheff, F. R. A. J. Rose, Journal of Pharmaceutical Sciences, 2008, 1-9; Y. M. Kwon, S. W. Kim Macromolecular Symposia, 201, 2003, 179-186; B. Jeong, Y. H. Bae, S. W. Kim, Journal of Controlled Release, 63, 2000, 155-163, C. He, S. W. Kim, D. S. Lee, Journal of Controlled Release, 127, 3, 2008, 189-207). The gels formed at temperatures close to human body temperature, thus could be used for injectable drug delivery systems. Another approach to prepare temperature sensitive hydrogels is based on the polymer having lower critical solution temperature. Vermonden et al (T. Vermonden, N. A. M. Besseling, M. J. Van Steenbergen, W. E. Hennink, Langmuir 2006, 22, 10180) prepared triblock (ABA) copolymers containing thermosensitive poly(N-(2-hydroxy propyl)methacryl amide lactate as block A and hydrophilic poly(ethylene glycol) as block B. Triblock polymers gelled rapidly on increasing the temperature to body temperature, which makes them suitable for injectable drug delivery systems. In yet another approach, supramolecular complex of polymer with cyclodextrin has been used to prepare in situ gels. Li et al (J. Li, X. Ni, K. W. Leong, Journal of Biomedical Materials Research, 65A, 2003, 196-202) investigated hydrogels resulting from the supramolecular self assembly comprising poly(ethylene oxide) s and α-cyclodextrin. The rheological data showed that the gels were thixotropic and reversible. In another work, Manakker et al (F. van de Manakker, M. van der Pot, T Vermonden, C. F. van Nostrum, W. E. Hennink, Macromolecules 41, 2008, 1766-1773) prepared poly(ethylene glycol) hydrogel based on inclusion complexes between β-cyclodextrin and cholesterol. The rheological studies showed that the hydrogels were thermoreversible. Physical crosslinking through hydrophobic interactions can also be achieved by thermogelling the ionic polymer solutions such as chitosan solutions in the presence of counterionic salts such as β-glycerophosphate or ammonium hydrogen phosphate (E. Ruel-Gariepy, M. Shive, A. Bichara, M. Berrada, D. L. Garrec, A. Chemte, J. Leroux, European Journal of Pharmaceutics and Biopharmaceutics 57, 2004, 53-63; and L. S, Nair, T. Starnes, J K. Ko, C. T. Laurencin, Biomacromolecules 8, 2007, 3779-3785). The gelling time at body temperature varied from 5 min to 30 hours depending upon the concentration of ammonium hydrogen phosphate.

Two polymers containing complementary stereoregular groups when mixed together under appropriate conditions can form hydrogel. Aqueous solution of L-lactic acid oligomers and D-lactic acid oligomers grafted individually onto dextran, when mixed together at room temperature undergo gelation by stereocomplexation (S. R. Van Tomme, A. Mens, C. F. van Nostrum, and W. E. Hennink, Biomacromolecules, 9, 2008, 158-165; G. W. Bos, J. J. L. Jacobs, J. W. Koten, S. van Tomme, T. Veldhuis, C. F. van Nostrum, W. D. Otter, W. E. Hennink, European Journal of Pharmaceutical Sciences 21, 2004, 561-567). The properties of the hydrogel varied with solid content of the gel, degree of substitution of lactic acid oligomers and degree of polymerization of oligolactate graft. Hiemstra et al (C. Hiemstra, Z. Zhong, L. Li, P. J. Dijkstra, J. Feijen, Biomacromolecules 7, 2006, 2790-2795) synthesized stereo complexed hydrogels by mixing eight arm poly(ethylene glycol)-poly(L-lactate) and poly(ethylene glycol)-poly(D-lactate). The concentration of the polymer in the solution governed storage modulus and gelation time.

The two well known disadvantages of physically crosslinked hydrogels are that their mechanical properties are weaker compared to chemically crosslinked hydrogels. Further any change in external environment such as pH, temperature and ionic strength may disturb the inherent interaction, causing the disruption of the gel. To prepare hydrogels which do not revert to sol form in the external environment, a chemical crosslinking approach is needed. Chemical crosslinking methods include photocrosslinking, redox initiation, complementary group crosslinking and condensation reactions.

Photopolymerisation methods involve the irradiation of polymer solution with visible or UV light to form an in situ network in the presence of a photoinitiator. Polymers containing acrylate and methacrylate groups undergo rapid crosslinking upon irradiation with UV light. The system that has been largely explored using photopolymerisation technique is a triblock system, which consists of poly(ethylene glycol) block flanked with biodegradable oligo block bearing terminal acrylate functionality (K. S. Anseth, A. T. Metiers, S. J. Bryant, P. J. Martens, J. H. Elisseeff, C. N. Bowman, Journal of Controlled Release 78, 2002, 199-209; T. Matsuda, M. Mizutani, Journal of Biomedical Materials Research 62, 2002, 395-403). The biodegradable blocks used are oligo caprolactone, oligo lactide and oligo glycolide. The triblock containing terminal acrylate functionality, rapidly crosslinked under visible or UV light in the presence of photoinitiator. Degradation time of the gel varied with the molecular weight of the biodegradable component used. Recently, there have been attempts to prepare supramolecular complex of the triblock macromonomer having terminal double bond and alpha-cyclodextrin (S. Zhao, L. Zang, D. Ma, C. Yang, L. Yan Journal of Physical Chemistry B 110, 2006, 16503-16507; F. Zeng-guo, Z. Sanping, Polymer 44, 2003, 5177-5186). The inclusion complex was subsequently photopolymerised in the presence of photoinitiator to obtain a biodegradable hydrogel. The combination of physical crosslinking through supramolecular complex and chemical crosslinking through photocrosslinking led to a hydrogel having high mechanical strength. Wei and colleagues (H. Wei, H. Yu, A. Zhang, L. Sun, D. Hou, Z. Feng, Macromolecules 38, 2005, 8833-8839) prepared a thermosensitive, supramolecular structured hydrogel by copolymerization of N-isopropylacrylamide with alpha-cyclodextrin threaded amphiphilic LA-PEG-LA copolymer end capped with a methacrylate group. The thermosensitivity of these hydrogels was modulated by varying the N-isopropyl-acrylamide content as well as the alpha-cyclodextrin to amphiphilic macromer ratio. In another attempt, oligomeric poly(2-hydroxyethylmethacrylate) and poly(N,N,-dimethyl acrylamide) were grafted onto hyaluronic acid followed by modification with glycidyl methacrylate (X. Jia, J. A. Burdick, J. Kobler, R. J. Clifton, J. J. Rosowski, S. M. Zeitels, R. Langer, Macromolecules 37, 2004, 3239-3248). The aqueous solution of macromonomer was photopolymerised in the presence of photoinitiator to obtain the gel. When compared with hyaluronic acid reacted with glycidyl methacrylate, the modified gel was resistant to enzymatic degradation and lower swelling. Doulabi et al (A. S. H. Doulabi, H. Mirzadeh, M. Imani, S. Sharifi, M. Atai, S. Mehdipour-Ataie, Polymers In Advanced Technologies, 2008) reported in situ formed devices based on biodegradable macromer comprising poly(ethylene glycol) and fumaric acid copolymers. The macromers were photocrosslinked for 300 seconds in the presence of visible light, initiator, accelerator and a reactive diluent. The use of N-vinylpyrrolidone as a reactive diluent increased the crosslink density and shrinkage strain.

The other method to prepare chemically crosslinked hydrogel at room temperature is by free radical polymerization using redox initiators. Franssen et al (O. Franssen, R. D. van Ooijen, D. de Boer, R. A. A. Maes, W. E. Hennink, Macromolecules 32, 1999, 2896-2902) synthesized dextran methacrylate based gel with redox initiators such as N,N,N, N-tetramethylethylenediamine and potassium peroxodisulfate. The aqueous solution of initiator and dextran methacrylate formed gel overnight at room temperature. The enzymatic degradability of the gel was studied with dextranase. Holland et al (T. A. Holland, J. K. V. Tessmar, Y. Tabata, A. G. Mikos Journal of controlled release 94, 2004, 101-114) studied the degradation and TGF release from gelatin microparticles embedded in biodegradable oligo-poly(ethylene glycol) fumarate network. The crosslinked hydrogel was prepared by reacting oligo-poly(ethylene glycol) fumarate with methylene biscrylamide using redox initiators tetramethylethylene diamine and ammonium persulfate. The hydrogel formed in 10 minutes at 37° C. An intelligent and biodegradable hydrogel was prepared by crosslinking temperature sensitive triblock poly(ethylene oxide)-poly(propylene oxide)-poly(ethylene oxide) with extension along each ends with oligo caprolactone terminated with acrylate group (B. Wang, W. Zhu, Y. Zhang, Z. Yang, J. Ding, Reactive and Functional Polymers 66, 2006, 509-518). The acrylate terminated macromer was dissolved in water and crosslinked using redox initiators tetramethylethylene diamine and ammonium persulfate. The hydrogel showed reversible temperature sensitive swelling/deswelling characteristics. Other groups have prepared hydrogels by chemical crosslinking of functional groups by condensation of a water soluble polymer with appropriate reactive reagents such as diisocyanates, glutaraldehyde and carbodiimides (U.S. Pat. No. 5,078,744; Tomihata, K, Ikada, Y., Journal of Polymer Science, Part A: Polymer Chemistry 35, 1997, 3553-3559; Tomihata, K; Ikada, Y., Journal of Biomedical Materials Research 37, 1997, 243-251). Eiselt et al (P. Eiselt, K. Y. Lee, D. J. Mooney, Macromolecules 32, 1999, 5561-5566) prepared alginate hydrogels with poly(ethylene glycol)diamine using 1-ethyl-3-(dimethyl aminopropyl)carbodiimide (EDC). Hydrogels of alginate with poly(ethylene glycol)diamines of different molecular weights were investigated to generate materials with a range of mechanical properties. However, these chemically crosslinked networks suffer from various limitations, such as the use of photoirradiation, the presence of residues of initiators, organic solvents and other reagents. The presence of such impurities is generally not acceptable in biomedical applications.

In order to overcome above mentioned limitations, chemical crosslinking of complementary groups has been studied. Recently, hydrogels formed from the chemical reaction of low molecular weight amines with N-hydroxysuccinimide based crosslinker groups was reported (Pub. No. US2009/0324721). However the limitations of this system include the loss of reactivity of functional groups during reaction and storage due to hydrolysis, incorporation of extended biodegradable region (extra synthetic engineering required) and the use of low molecular weight amines (high probability of leaching out to the surrounding during crosslinking). Another way of preparing hydrogel using chemical crossing of complementary groups is the reaction of thiol with vinyl moieties. Hiemstra et al (C. Hiemstra, L. J. van der Aa, Z. Zhong, P. J. Dijkstra, J. Feijen, Macromolecules 40, 2007, 1165-1173; C. Hiemstra, Z. Zhong, M. J. van Steenbergen, W. E. Hinnink, J. Feijen, Journal of Controlled Release 122, 2007, 71-78) synthesized various vinylsulfone containing dextrans and reacted with multi functional poly(ethylene glycol) having thiol group. Hydrogel formed rapidly upon mixing in aqueous medium under physiological condition. The degradation time of the gel varied from 3 to 21 days. Besides dextran, hyaluronic acid has also been reported to form in situ gels. Shu et al (X. Z. Shu, Y. Liu, F. S. Palumbo, Y. Luo, G. D. Prestwich, Biomaterials 25, 2004, 1339-1348) reported two thiolated hyaluronan derivatives coupled to four α,β-unsaturated esters and amides. It was disclosed that the gelation time varied from 10 minutes to 2 hrs. Subsequently, Vanderhooft et al (J. L. Vanderhooft, B. K. Mann, G. D. Prestwich, Biomacromolecules 8, 2007, 2883-2889) synthesized novel thiol reactive poly(ethylene glycol) crosslinkers to prepare hydrogel with thiol mediated derivative of hyaluronan. The gelation time at physiological pH varied from 1 minute to over 2 hrs. Hydrogel mimics of extracellular matrix were synthesized by crosslinking thiol modified analog of heparin and thiol modified hyaluronan with polyethylene glycol diacrylate (S. Cai, Y. Liu, X. Z. Shu, G. D. Prestwich Biomaterials 26, 2005, 6054-6067). The water content of the hydrogel was more than 97% and gelation occurred within 10 minutes. Similarly, hyaluronic acid based gels were prepared by Kim et al (G. Kim, Y. Choi, M. Kim, Y. Park, K. Lee, I. Kim, S. Hwang, I. Noh, Current Applied Physics 7SI, 2007, e28-e32) using aminopropylmethacrylate modified hyaluronic acid and multifunctional poly(ethylene glycol) with thiol groups. Thiol functionalization was also utilized to prepare poly(vinyl alcohol) based hydrogel for in vitro retinal replacement surgery (M. Tortora, F. Cavalieri, E. Chiessi, G. Paradossi Biomacromolecules 8, 2007, 209-214). The hydrogel was formed by the reaction of thio capped poly(vinyl alcohol) with methacrylate derivative of poly(vinyl alcohol). Poly(vinyl alcohol) hydrogel gelled in 60 minutes at physiological condition in aqueous medium. Qiu et al (B Qiu, S. Stefanos, J. Ma, A. Lalloo, B. A. Perry, M. J. Leibowitz, P. J. Sinko, S. Stein, Biomaterials 24, 2003, 11-18) described a hydrogel from poly(ethylene glycol) based copolymer with multifunctional thiol and divinyl sulfone poly(ethylene glycol). The aqueous mixture of the composition formed a gel in 2-3 minutes. A major disadvantage of the system is the fate of thiol group during storage and application, as thiol groups are known to be oxidized to disulfide by oxygen. Moreover thiol compounds are known to degrade the disulfide bond present in the protein, leading to denaturation. Again the variation in degradation time of the gel is brought about by sacrificing the crosslinking density.

References may be made to an article "D. M. Lynn, D. G. Anderson, D. Putnam, R. Langer, Journal of the American Chemical Society 123, 2001, 8155-8156" wherein the synthesis of poly(β-aminoester) by the addition of amine to diacrylate ester has been described. Further, WO2004/106411 discloses a method for synthesizing poly(beta-amino esters) prepared from the addition of bis(secondary amines) or primary amines with bis(acrylate ester) in an organic solvent, wherein the amine is in the form of polynucleotide/polymer complexes (DNA/polymer concentration) and polyethylene glycol polymers. U.S. Pat. No. 6,998,115 discloses a method for preparation of the polymers, specifically the poly β-amino esters and salts which are useful for the drug delivery devices and pharmaceutical composition. The poly β-amino esters are prepared by the conjugate addition of bis(secondary amines) or primary amines to bis(acrylate ester). The monomers are dissolved in an organic solvent such as methylene chloride and the resulting solution is further combined and heated for the polymerization of the said monomers. The polymerization time was 5 days at 45° C.

References may be made to patent WO2008/011561, wherein end-modified poly(beta-amino esters) prepared by the addition of a nucleophilic reagent (e.g., an amine) to an acrylate-terminated poly(beta-amino ester) which are useful in a variety of medical applications including drug delivery, tissue engineering, and biomaterials and non-medical applications including coatings, plastics, paints, and films are disclosed. Further, the invention discloses a method of synthesizing an end-modified poly(β-amino ester), comprising following steps: a) providing an amine-terminated poly(β-amino ester); b) providing an acrylate; and c) reacting the acrylate and the amine-terminated poly(β-amino ester) under suitable conditions to form an end-modified poly(β-amino ester). The polymerization time was typically 24 hrs at 90° C. for the preparation of acrylate modified poly(β-amino esters).

Recently, a combinatorial library of photocrosslinkable and degradable poly(β-aminoester) was synthesized and evaluated (D. G. Anderson, C. A. Tweedie, N. Hossain, S. M. Navarro, D. M. Brey, K. J. Van Vliet, R. Langer, J. A. Burdick, Advanced Materials 18, 2006, 2614-2618). Macromers of different molecular weight and chemical structures bearing a terminal acrylate group were synthesized by the reaction of excess diacrylates with primary or bis(secondary) amines. The macromers were photopolymerised with UV lamp in the presence of photoinitiator 2,2-dimethoxy-2-phenylacetophenone dissolved in 10 wt % of dichloromethane. The library of 120 poly(β-aminoester) (PBAE) networks exhibited a wide range of degradation behaviour with mass loss of 100% within 24 hrs to little mass loss even after 57 days of immersion. These variations were brought about by simple variation in diacrylate and amines used. Brey et al (D. M. Brey, J. L. Ifkovits, R. I. Mozia, J. S. Katz, J. A. Burdick, Acta Biomaterialia 4, 2008, 207-217) disclosed a large library of PBAEs, synthesized via a step growth polymerization of liquid amines and diacrylates developed for biomaterial applications. The said article also disclosed and synthesized a macromer system, with a variety of branching structures, to illustrate the diverse properties possible through this structural variation. The system involves the synthesis, from a diacrylate (E) and a primary amine to form a linear diacrylated macromer, or alternatively, a system of branched multiacrylated and linear diacrylated macromers with the addition of small quantities of triacrylate (PETA). The macromers were dissolved in methylene chloride and photopolymerised in the presence of a photoinitiator 2,2-dimethoxy-2-phenylacetophenone to obtain poly(β-amino ester) networks. The increase in macromer branching improved the gel content and mechanical properties of the networks.

References may be made to journal "T. Kim, H. J. Seo, J. S. Choi, J. K. Yoon, J. Back, K. Kim, J. Park, Bioconjugate Chemistry 16, 2005, 1 140-1 148" and "J. Kloeckner, E. Wagner, M. Ogris, European Journal of Pharmaceutical Sciences 29, 2006, 414-425" wherein biodegradable crosslinked poly(β-aminoester) synthesized directly by conjugate addition of diacrylates with amines in different organic solvents at 50-60° C. for 2-4 days has been reported.

The current strategies for the synthesis of crosslinked poly (β-aminoester) networks include use of photo polymerization and/or thermal curing. However, these crosslinked networks suffer from many limitations, such as the use of photoirradiation, the presence of residual initiators, organic solvents, other reagents, high reaction temperature and high reaction times. After conducting several laboratory scale methods it is surprisingly found that aqueous solutions containing water soluble diacrylates and aqueous solutions containing multifunctional amines, when mixed together react rapidly and yield hydrogels. Since, the gelation temperature is close to human body temperature, the technique can be used to synthesize in situ formed hydrogels which further degrade under physiological conditions.

SUMMARY OF THE INVENTION

The main objective of the present invention is to provide biodegradable hydrogels which can be effected in aqueous medium even at body temperature eliminating the need for any external catalysts.

Another object of the invention is to provide biodegradable hydrogels where the swelling degradability of the gels can be easily altered.

One more object of the invention is to provide biodegradable hydrogels where the time for the in situ gel formation can be varied from few minutes to hours.

Yet another object of the invention is to provide biodegradable hydrogels where the properties of gels can be tailored over a wide range.

Another object of the invention is to provide a method for in situ synthesis of hydrogels.

Accordingly, present invention provides a fast curing biodegradable polymeric hydrogel composition comprising a component A and component B forming a β-aminoester linkage such that the linkage results in gelation at temperatures in the range of 25-55° C. wherein component A is water soluble polymer containing acrylate functionality and component B is a water soluble polymer containing amine.

In an embodiment of the present invention, the component A is a biodegradable water soluble polymer containing acrylate functionality.

In an another embodiment of the present invention, the component B is a biodegradable polymer containing amine functionality.

In yet another embodiment of the present invention, component A is selected from poly(ethylene glycol)diacrylate (PEGDA) of molecular weight in the range of 200 to 2500 Da or acrylate derivative of poly(hydroxyethyl aspartamide) (PHEAAC) of molecular weight in the range of 5000 to 22,000 Da.

In yet another embodiment of the present invention, acrylate modification in said acrylate derivative of poly(hydroxyethyl aspartamide) (PHEAAC) is in the range of 5 to 53 mole %.

In an another embodiment of the present invention, the amine functionality is selected from the group consisting of amine terminated poly(ethylene glycol), poly(succinimide) containing amine functionality, poly(amino ester) containing amine, and amino acid.

In yet another embodiment of the present invention, water soluble amine B is an amine terminated poly(ethylene glycol) of molecular weight in the range of 200 to 2500 Da.

In yet another embodiment of the present invention, the water amine B is poly(succinimide) containing amine functionality wherein amine functionality is selected from primary or secondary amine.

In yet another embodiment of the present invention, the primary functionality modification is selected from ethylenediamine, 1,3-diamino propane and hexamethylenediamine.

In yet another embodiment of the present invention, the secondary amine modification is piperazine.

In yet another embodiment of the present invention, the water soluble multifunctional amine B is poly(amino ester) containing secondary amine functionality.

In yet another embodiment of the present invention secondary amine functionality is 1-(2-aminoethyl)piperazine.

In yet another embodiment of the present invention, the molecular weight of poly(amino ester) containing secondary amine functionality is in the range of 6,000 to 10,000 Da.

In yet another embodiment of the present invention, the multifunctional amine B is an amino acid.

In yet another embodiment of the present invention, said amino acid is lysine.

In yet another embodiment of the present invention, the gelation time of the hydrogel is ranges between 10 seconds to 5 hours, preferably 10 seconds to 45 minutes.

In yet another embodiment of the present invention, the biodegradation time of the hydrogels is from 1.5 hour to 55 days.

Another aspect of the present invention is a process for the synthesis of biodegradable hydrogel as claimed in claim 1, wherein the process comprises
a) reacting component A and component B in aqueous medium in the temperature range of 25 to 55° C. until gelation takes place,
b) optionally mixing component A and/or component B in non aqueous medium prior to step (a) and,
c) optionally drying the hydrogel formed.

In yet another embodiment of the present invention, the gelation is carried out at temperature in the range 30 to 40° C.

In yet another embodiment of the present invention, the hydrogel is dried by tray drying, vacuum drying or freeze drying.

In yet another embodiment of the present invention, the components A and B are mixed with each other and dispersed in a non-aqueous medium prior to gelation, raising the temperature to up to 55° C. to form gel beads.

In yet another embodiment of the present invention, the solution comprising component A and component B is cast in the form of a film, raising the temperature up to 55° C. and curing the film.

In yet another embodiment of the present invention, an aqueous solution of A is coated on a substrate and an aqueous solution of B is applied as a coating above said coat of A, raising the temperature to up to 55° C. and gelling the coating.

In yet another embodiment of the present invention, said process comprises of dispersing component B in a solution of component A in N-methylpyrrolidone, dumping the dispersion in aqueous medium and raising the temperature to 40° C. until gelation takes place.

In yet another embodiment of the present invention, said process comprises of dispersing component B and component A in N-methyl pyrrolidone, dumping the dispersion in aqueous medium and raising the temperature to 40° C. until gelation takes place.

In yet another embodiment of the present invention, said composition is useful as biomaterials for medical applications such as drug delivery and tissue engineering.

DETAILED DESCRIPTION OF THE INVENTION

Figure 1:
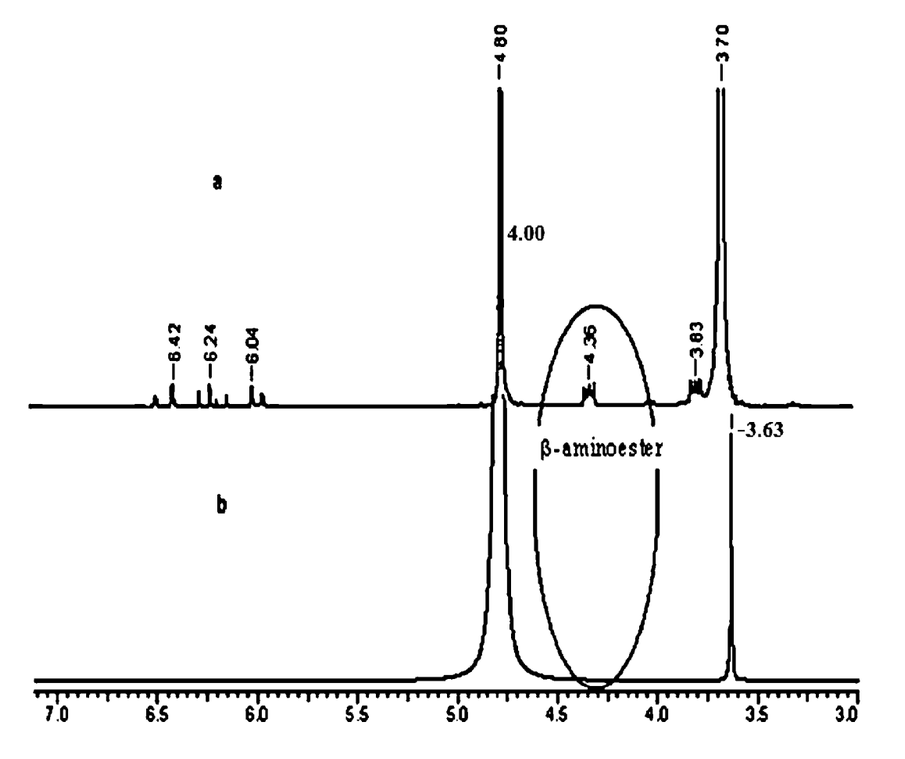
FIG. 1 represents $^{1}H$-NMR spectra of a) PEGDA2110, and b) degradation byproducts of hydrogel of PSIPIP (Poly(succinimide) modified with piperazine) crosslinked with PEGDA2110.

The present invention provides a fast curing biodegradable polymeric hydrogel composition comprising a component A and component B forming a β-aminoester linkage such that the linkage results in gelation at temperatures in the range of 25-55° C., wherein component A is water soluble polymer containing acrylate functionality and component B is a water soluble multifunctional amine functionality.

The present invention provides in situ forming hydrogels based on poly(β-aminoester). The present invention also provides a method for in situ synthesis of hydrogels which can be synthesized in aqueous medium at body temperature eliminating the need of any external catalysts.

The present invention further provides a method for preparation of the hydrogel involving in situ polymerization of component A and component B in aqueous medium without using any catalyst, in the temperature range 20 to 60° C. and optionally drying the hydrogel formed.

The present invention provides a fast curing biodegradable hydrogel composition comprising a water soluble component A and a water soluble amine B forming a β-aminoester linkage in an aqueous medium.

The said water soluble component A is selected from poly (ethylene glycol)diacrylate (PEGDA) (Mil=200-2,500 Da) and acrylate derivative of poly(hydroxyethyl aspartamide) (PHEAAC). The extent of acrylate modification in the acrylate derivative of poly(hydroxyethyl aspartamide) is in the range 5 to 53 mole %. The molecular weight of PHEAAC is in the range 5,000 to 22,000 Da.

The water soluble multifunctional amine B is an amine terminated poly(ethylene glycol) wherein molecular weight of poly(ethylene glycol) is in the range 200 to 2,500 Da and is preferably poly(ethylene glycol)diacrylate modified with ethylenediamine.

The water soluble multifunctional amine B is a biodegradable polymer containing amine functionality, poly(succinimide) containing amine functionality wherein amine functionality can be primary amine or secondary amine.

The water soluble multifunctional amine B is a biodegradable poly(amino ester) containing secondary amine functionality. The molecular weight of poly(amino ester) containing secondary functionality is in the range 6000 to 10000 Da.

The water soluble multifunctional amine B is an amino acid, lysine.

In the preferred embodiment, the process for the synthesis of biodegradable hydrogel involves mixing component A and component B in aqueous medium in the temperature range 25 to 55° C. until gelation takes place and optionally drying the hydrogel formed.

The gelation time varies between 10 seconds to 5 hrs. The hydrogel is dried by tray drying, vacuum drying or freeze drying.

Alternatively, the components A and B are mixed with each other and dispersed in a nonaqueous medium prior to gelation, raising the temperature up to 55° C. to form the gel beads.

In another preferred embodiment, an aqueous solution of A is coated on a substrate and an aqueous solution of B is applied as a coating above it raising the temperature up to 55° C., and gelling the coating.

In another embodiment, the solution comprising component A and component B is cast in the form of a film, raising the temperature up to 55° C. and curing the film.

In the preferred embodiment, the process for the synthesis of biodegradable hydrogel involves dispersing component B in a solution of component A in N-methylpyrrolidone and then dumping the same in aqueous medium, raising the temperature to 40° C. until gelation takes place.

Alternatively, the components A and B are dispersed in N-methylpyrrolidone and then dumping the same in aqueous medium, raising the temperature to 40° C. to form hydrogel.

In another embodiment, the gelation takes place rapidly in aqueous medium which eliminates the drawback of the conventional systems wherein the presence of residual organic solvents and other additives such as catalysts is unacceptable because of deleterious effect on product performance.

The gel time could be varied from 10 seconds to 45 minutes at 37° C. The degradation and swelling time can be tailored to meet the desired performance requirement by choosing appropriate precursors A and B. According to the choice of the components A and B, the degradation time of the gel varied from 1.5 hour to 55 days.

The said hydrogel will be more useful in a variety of medical applications including drug delivery and tissue engineering. The controlled drug delivery includes oral, mucosal, as well as injectable drug delivery systems.

EXAMPLES

The following examples are given by way of illustration only and therefore should not be construed to limit the scope of the present invention.

Characterization

The molecular weights of the hydrogel precursors were determined by aqueous gel permeation chromatography and Vapour Pressure Osmometry (VPO), using chloroform as solvent. The gel time was determined by test tube invertion method.

The water content (W, %) of the system was determined by the equation $$W = \frac{W_2 - W_1}{W_2} \times 100$$

where:
W2 is the weight of the swollen hydrogel (maximum weight),
W1 is the weight of the polymer precursors used.

In vitro degradation studies were done as follows. Solutions of hydrogel precursors in 7.4 pH phosphate buffer were mixed at 37° C. to form gels. These gels were immersed in 7.4 pH phosphate buffer and incubated at 37° C. until they dissolved. The time required for complete dissolution of the gels was termed as hydrogel degradation time.

Example 1

Synthesis of Hydrogel from Amine Modified Poly(Ethylene Glycol)Diacrylate and Poly(Ethylene Glycol)Diacrylate (PEGDA)($M_n$=700)

Amine Modified Poly(Ethylene Glycol)Diacrylate (PEGDADA)

End modified poly(ethylene glycol)diacrylate ($M_n$=700) was synthesized by reacting PEGDA with excess of ethylenediamine. 5 g of PEGDA in 10 ml dichloromethane (DCM) was added to a solution of 7 ml ethylenediamine in 10 ml dichloromethane with stirring. After complete addition the mixture was stirred using magnetic stirrer over 12 hrs at 25° C. The solution was poured into a mixture of diethylether/ethanol (90/10) to obtain viscous amine capped PEGDA (PEGDADA). The macromer was stored at 5° C.

Hydrogel Preparation 0.039 g of amine modified polyethylene glycol diacrylate (PEGDADA) dissolved in 100 µl of phosphate buffer at pH 7.4 was mixed with 0.100 g of PEGDA ($M_n$=700). The mixture was incubated at 37° C. in a water bath to form hydrogel. The gel time, water content and hydrogel degradation time are described in Table 1.

Example 2

Synthesis of Hydrogel from Amine Modified Poly(Ethylene Glycol)Diacrylate and Poly(Ethylene Glycol)Diacrylate (PEGDA)($M_n$=258)

0.105 g of amine modified poly(ethylene glycol)diacrylate dissolved in 100 µl of phosphate buffer at pH 7.4 was mixed with 0.100 g of PEGDA ($M_n$=258). The mixture was incubated at 37° C. in a water bath to form hydrogel. The gel time, water content and hydrogel degradation time are described in Table 1.

Example 3

Synthesis of hydrogel from poly(amino ester)s (1,4-butanediol diacrylate and 1-(2-aminoethyl)piperazine) and Poly(ethylene glycol)diacrylate (PEGDA) ($M_n$=700)

Synthesis of poly(amino ester)s from 1,4-butanediol diacrylate and 1-(2-aminoethyl)piperazine (PAEPBDDA)

2 g of 1,4-butanediol diacrylate in 20 ml of chloroform was added dropwise to a solution of 1.3035 g of 1-(2-aminoethyl) piperazine in 15 ml of chloroform under stirring at 25° C. for a period of one hour. After completion of addition, the reaction temperature was increased to 45° C. The reaction mixture was stirred at 45° C. for 3 days. The solution was concentrated and precipitated in diethylether to obtain a water soluble poly(amino ester). The molecular weight of the polymer was determined by Vapour Pressure Osmometry and is summarized in Table 2.

Hydrogel Preparation 0.100 g of PAEPBDDA dissolved in 200 µl of phosphate buffer at pH 7.4 was mixed with 0.107 g of PEGDA. The mixture was incubated at 37° C. in a water bath to form hydrogel. The gel time, water content and hydrogel degradation time are described in Table 1.

Example 4

Synthesis of hydrogel from poly(amino ester)s (1,4-butanediol diacrylate and 1-(2-aminoethyl)piperazine) and Poly(ethylene glycol)diacrylate (PEGDA) ($M_n$=258)

0.100 g of PAEPBDDA was dissolved 200 µl phosphate buffer at pH 7.4 and was mixed with 0.039 g of PEGDA. The mixture was incubated at 37° C. in a water bath to form hydrogel. The gel time, water content and hydrogel degradation time are described in Table 1.

Example 5

Synthesis of hydrogel from poly(amino ester)s (Poly(ethylene glycol)diacrylate (PEGDA) ($M_n$=258) and 1-(2-aminoethyl)piperazine) and Poly(ethylene glycol)diacrylate (PEGDA) ($M_n$=700)

Synthesis of poly(amino ester)s from poly(ethylene glycol)diacrylate (PEGDA) ($M_n$=258) and 1-(2-aminoethyl)piperazine (PAEPPEG)

2 g of poly(ethylene glycol)diacrylate (PEGDA) ($M_n$=258) in 20 ml of chloroform was added dropwise to a solution of 1.0015 g of 1-(2-aminoethyl)piperazine in 15 ml of chloroform under stirring at 25 C for a period of one hour. After completion of addition, the reaction temperature was increased to 45° C. The reaction mixture was stirred at 45° C. for 3 days. The solution was concentrated and precipitated in diethylether to obtain a water soluble poly(amino ester). The molecular weight of the polymer was determined by Vapour Pressure Osmometry and is summarized in Table 2.

Hydrogel Preparation 0.100 g of PAEPPEG dissolved in 200 µl of phosphate buffer at pH 7.4 was mixed with 0.090 g of PEGDA ($M_n$=700). The mixture was incubated at 37° C. in a water bath to form hydrogel. The gel time, water content and hydrogel degradation time are described in Table 1.

Example 6

Synthesis of Hydrogel from Ethylenediamine Modified Polysuccinimide (PSIED) and Poly(Ethylene Glycol)Diacrylate (PEGDA) ($M_n$=700)

Synthesis of Polysuccinimide (PSI)

50 g of L-Aspartic acid and 5.7 g of 87% phosphoric acid were placed in a round bottom flask under nitrogen atmosphere. The system was mixed while raising the temperature to 200° C. The thermal polycondensation reaction was done over a period of 7 hours. The product was dissolved in 200 ml of dimethylformamide and precipitated in 2.5 L of distilled water. The precipitate was filtered, washed several times with methanol and dried at 85° C. for 24 hrs to yield polysuccinimide.

Synthesis of Ethylenediamine Modified Polysuccinimide (PSIED)

2 g of polysuccinimide in 40 ml of dimethylformamide was added dropwise to a solution of 16 g of ethylenediamine in 200 ml of dimethylformamide under stirring at 0° C. for a period of 4 hrs. The reaction mixture was then stirred for another 4 hrs at 25° C. The solution was precipitated in a mixture of 1:0.5 diethylether/ethanol. The precipitate was washed three times with diethylether/ethanol mixture. The filtered precipitate was dissolved in deionized water and centrifuged. The aqueous solution was dialysed using a dialysis bag for 24 hrs. After dialysis, the solution was freeze dried to obtain ethylenediamine modified Polysuccinimide.

Hydrogel Preparation

Synthesis of Hydrogel from Poly(Ethylene Glycol)Diacrylate ($M_n$=700) and Ethylenediamine Modified Polysuccinimide 0.100 g of PSIED dissolved 400 µl phosphate buffer at pH 7.4 was mixed with 0.4455 g of PEGDA. The mixture was incubated at 37° C. in a water bath to form hydrogel. The gel time, water content and hydrogel degradation time are described in Table 1.

Example 7

Synthesis of hydrogel from 1,3-diaminopropane modified Polysuccinimide (PSIDP) and Poly(ethylene glycol)diacrylate (PEGDA) ($M_n$=700)

Synthesis of 1,3-diaminopropane modified Polysuccinimide (PSIDP)

2 g of polysuccinimide in 60 ml of dimethylformamide was added dropwise to a solution of 20 g of 1,3-diaminopropane in 200 ml of dimethylformamide under stirring at 0° C. for a period of 4 hrs. The reaction mixture was then stirred for another 4 hrs at 25° C. The solution was precipitated in a mixture of 1:0.5 diethylether/ethanol. The precipitate was washed three times with diethylether/ethanol mixture. The filtered precipitate was dissolved in deionized water and centrifuged. The aqueous solution was dialysed using a dialysis bag for 24 hrs. After dialysis, the solution was freeze dried to obtain 1,3-diaminopropane modified polysuccinimide.

Hydrogel Preparation 0.100 g of PSIDP dissolved in 400 µl phosphate buffer at pH 7.4 was mixed with 0.4090 g of PEGDA. The mixture was incubated at 37° C. in a water bath to form hydrogel. The gel time, water content and hydrogel degradation time are described in Table 1

Example 8

Synthesis of Hydrogel from Hexamethylenediamine Modified Polysuccinimide (PSIHD) and Polyethylene Glycol)Diacrylate (PEGDA) ($M_n$=700)

Synthesis of Hexamethylenediamine Modified Polysuccinimide (PSIHD)

2 g of polysuccinimide in 50 ml of dimethylformamide was added dropwise to a solution of 22 g of hexamethylenediamine in 150 ml of dimethylformamide under stirring at 25° C. for a period of 4 hrs. The reaction mixture was then stirred for another 20 hrs at 25° C. The solution was precipitated in a mixture of 1:0.5 diethylether/ethanol. The precipitate was washed three times with diethylether/ethanol mixture. The filtered precipitate was dissolved in deionized water and dialysed using a dialysis bag for 24 hrs. After dialysis, the solution was freeze dried to obtain hexamethylenediamine modified polysuccinimide.

Hydrogel Preparation

Synthesis of Hydrogel from Hexamethylenediamine Modified Polysuccinimide (PSIHD) and Polyethylene Glycol)Diacrylate (PEGDA) ($M_n$=700) (1:1 mole %)

0.100 g of PSIHD dissolved in 400 µl of phosphate buffer at pH 7.4 was mixed with 0.3283 g of PEGDA. The mixture was incubated at 37° C. in a water bath to form hydrogel. The gel time, water content and hydrogel degradation time are described in Table 1.

Example 9

Synthesis of Hydrogel from Hexamethylenediamine Modified Polysuccinimide (PSIHD) and Polyethylene Glycol)Diacrylate (PEGDA) ($M_n$=700) (1:0.20 mole %)

0.100 g of PSIHD dissolved in 400 µl phosphate buffer at pH 7.4 was mixed with 0.06566 g of PEGDA. The mixture was incubated at 37° C. in a water bath to form hydrogel. The gel time, water content and hydrogel degradation time are described in Table 1.

Example 10

Synthesis of Hydrogel from Piperazine Modified Polysuccinimide (PSIPIP) and Poly(Ethylene Glycol)Diacrylate (PEGDA) ($M_n$=700)

Synthesis of Piperazine Modified Polysuccinimide (PSIPIP)

2 g of polysuccinimide in 50 ml of dimethylformamide was added dropwise to a solution of 15 g of piperazine in 200 ml of dimethylformamide under stirring at 25° C. for a period of 4 hrs. The reaction mixture was then stirred for another 20 hrs at 25° C. The solution was precipitated in a mixture of 1:0.5 diethylether/ethanol. The precipitate was washed three times with diethylether/ethanol mixture. The filtered precipitate was dissolved in deionized water and dialysed using a dialysis bag for 24 hrs. After dialysis, the solution was freeze dried to obtain piperazine modified polysuccinimide. The molecular weight of the polymer was determined by aqueous gel permeation chromatography and is summarized in Table 3.

Hydrogel Preparation

Synthesis of Hydrogel from Piperazine Modified Polysuccinimide (PSIPIP) and Poly(Ethylene Glycol)Diacrylate (PEGDA) ($M_n$=700) (1:1 mole %)

0.100 g of PSIPIP dissolved in 400 µl of phosphate buffer at pH 7.4 was mixed with 0.191 1 g of PEGDA. The mixture was incubated at 37° C. in a water bath to form hydrogel. The gel time, water content and hydrogel degradation time are described in Table 1.

Example 11

Synthesis of Hydrogel from Piperazine Modified Polysuccinimide (PSIPIP) and Poly(Ethylene Glycol)Diacrylate (PEGDA) ($M_n$=700) (1:0.20 mole %)

0.100 g of PSIPIP dissolved in 400 µl phosphate buffer at pH 7.4 was mixed with 0.03822 g of PEGDA. The mixture was incubated at 37° C. in a water bath to form hydrogel. The gel time, water content and hydrogel degradation time are described in Table 1.

Example 12

Synthesis of Hydrogel from Piperazine Modified Polysuccinimide (PSIPIP) and Acrylate (5%) Derivative of Poly(Hydroxyethyl Aspartamide) (PHEAAC)

Synthesis of Poly(Hydroxyethyl Aspartamide) (PHEA3)

1.25 g of ethanolamine in 2 ml of dimethylformamide was added dropwise to a solution containing 2 g of polysuccinimide in 10 ml of dimethylformamide under stirring at 25° C. Subsequently, the reaction mixture was heated at 50° C. for a period of 24 hrs. The solution was then precipitated in excess of ethanol. The filtered precipitate was dissolved in deionized water and dialysed using a dialysis bag for 48 hrs. After dialysis, the solution was freeze dried to obtain PHEA3. The molecular weight of the polymer was determined by aqueous gel permeation chromatography. Poly(hydroxyethyl aspartamide) of different molecular weights was synthesized by reacting ethanolamine with various polysuccinimide and is summarized in Table 3.

Synthesis of Acrylate (5%) Derivative of Poly(Hydroxyethyl Aspartamide) (PHEAAC)

2 g of PHEA3 was dissolved in 40 ml of dimethylformamide under nitrogen atmosphere. Upon cooling to 0° C., 0.86 ml of triethylamine was added dropwise with stirring. Subsequently, 0.25 ml of acryloyl chloride dissolved in 15 ml of dimethylformamide was added dropwise with stirring under nitrogen atmosphere for a period of 4 hrs. The reaction mixture was stirred at 25° C. for another 48 hrs. The precipitated triethylamine salt was separated by filtration. The filtrate was precipitated in excess of diethylether. The filtered precipitate was washed with excess of dichloromethane and acetone to yield acrylate derivative of poly(hydro y ethyl aspartamide).

Hydrogel Preparation 0.0091 g of PSIPIP dissolved in 100 µl of phosphate buffer at pH 7.4 was mixed with 0.100 g of PHEAAC (5%) in 200 µl of phosphate buffer at pH 7.4. The mixture was incubated at 37° C. in a water bath to form hydrogel. The gel time, water content and hydrogel degradation time are described in Table 1.

Example 13

Synthesis of Hydrogel from Piperazine Modified Polysuccinimide (PSIPIP) and Acrylate (52%) Derivative of Poly(Hydroxyethyl Aspartamide) (PHEAAC)

Synthesis of Acrylate (52%) Derivative of Poly(Hydroxyethyl Aspartamide) (PHEAAC)

2 g of PHEA3 was dissolved in 50 ml of dimethylformamide under nitrogen atmosphere. Upon cooling to 0° C., 2.5 ml of triethylamine was added dropwise with stirring. Subsequently, 1.8 ml of acryloyl chloride dissolved in 20 ml of dimethylformamide was added dropwise with stirring under nitrogen atmosphere for a period of 4 hrs. The reaction mixture was stirred at 25° C. another 48 hrs. The precipitated triethylamine salt was separated by filtration. The filtrate was precipitated in excess of diethylether. The filtered precipitate was washed with excess of dichloromethane and acetone to yield acrylate derivative of poly(hydroxyethyl aspartamide).

Hydrogel Preparation 0.075 g of PSIPIP dissolved in 100 µl of phosphate buffer at pH 7.4 was mixed with 0.100 g of PHEAAC (52%) in 200 µl phosphate buffer at pH 7.4. The mixture was incubated at 37° C. in a water bath to form hydrogel. The gel time, water content and hydrogel degradation time are described in Table 1.

Example 14

Synthesis of Hydrogel from Hexamethylenediamine Modified Polysuccinimide (PSIHD) and Acrylate (5%) Derivative of Poly(Hydroxyethyl Aspartamide) (PHEAAC)

0.0053 g of PSIHD dissolved in 100 µl of phosphate buffer at pH 7.4 was mixed with 0.100 g of PHEAAC (5%) in 200 µl-phosphate buffer at pH 7.4. The mixture was incubated at 37° C. in a water bath to form hydrogel. The gel time, water content and hydrogel degradation time are described in Table 1.

Example 15

Synthesis of Hydrogel from Hexamethylenediamine Modified Polysuccinimide (PSIHD) and Acrylate (52%) Derivative of Poly(Hydroxyethyl Aspartamide) (PHEAAC)

0.044 g of PSIHD dissolved in 100 µl of phosphate buffer at pH 7.4 was mixed with 0.100 g of PHEAAC (52%) in 200 µl of phosphate buffer at pH 7.4. The mixture was incubated at 37° C. in a water bath to form hydrogel. The gel time, water content and hydrogel degradation time are described in Table 1.

Example 16

Synthesis of hydrogel from O,O'-Bis-(2-aminopropyl)polypropylene glycol-block-polyethylene glycol-block-polypropylene glycol (Mn=800) and acrylate (52%) derivative of poly(hydroxyethyl aspartamide) (PHEAAC)

0.1656 g of O,O'-Bis-(2-aminopropyl)polypropylene glycol-block-polyethylene glycol-block-polypropylene glycol (Mn=800) dissolved in 100 µl phosphate buffer at pH 7.4 was mixed with 0.100 g of PHEAAC (52%) in 200 µl phosphate buffer at pH 7.4. The mixture was incubated at 37° C. in a water bath to form hydrogel. The gel time, water content and hydrogel degradation time are described in Table 1.

Example 17

Synthesis of hydrogel from O,O'-Bis-(2-aminopropyl)polypropylene glycol-block-polyethylene glycol-block-polypropylene glycol (Mn=1900) and acrylate (52%) derivative of poly(hydroxyethyl aspartamide) (PHEAAC)

0.3933 g of O,O'-Bis-(2-aminopropyl)polypropylene glycol-block-polyethylene glycol-block-polypropylene glycol (Mn=1900) dissolved in 100 µl phosphate buffer at pH 7.4 was mixed with 0.100 g of PHEAAC (52%) in 200 µl phosphate buffer at pH 7.4. The mixture was incubated at 37° C. in a water bath to form hydrogel. The gel time, water content and hydrogel degradation time are described in Table 1.

Example 18

Synthesis of Hydrogel from Lysine and Poly(Ethylene Glycol)Diacrylate (PEGDA) ($M_n$=700)

0.02084 g of lysine dissolved in 200 µl of phosphate buffer at pH 7.4 was mixed with 0.200 g of PEGDA ($M_n$=700). The mixture was incubated at 37° C. in a water bath to form hydrogel. The gel time, water content and hydrogel degradation time are described in Table 1.

Example 19

Synthesis of Hydrogel from Lysine and Poly(Ethylene Glycol)Diacrylate (PEGDA) ($M_n$=575)

0.025 g of lysine dissolved in 200 µl phosphate buffer at pH 7.4 was mixed with 0.200 g of PEGDA ($M_n$=575). The mixture was incubated at 37° C. in a water bath to form hydrogel. The gel time, water content and hydrogel degradation time are described in Table 1.

Example 20

Synthesis of Hydrogel from Lysine and PHEAAC (Acrylate Content=52%)

0.030 g of PHEAAC dissolved in 100 µl phosphate buffer at pH 7.4 was mixed with 0.004 g of lysine. The mixture was incubated at 37° C. in a water bath to form hydrogel. The gel time, water content and hydrogel degradation time are described in Table 1.

Example 21

Synthesis of hydrogel from poly(amino ester)s (1,4-butanediol diacrylate and 1-(2-aminoethyl)piperazine) and poly(ethylene glycol)diacrylate (PEGDA) ($M_n$=700) at 25° C.

0.100 g of PAEPBDDA was dissolved 200 µl phosphate buffer at pH 7.4 and was mixed with 0.107 g of PEGDA. The mixture was incubated at 25° C. in a water bath to form hydrogel. The gel time of the hydrogel is described in Table 4.

Example 22

Synthesis of hydrogel from poly(amino ester)s (1,4-butanediol diacrylate and 1-(2-aminoethyl)piperazine) and Poly(ethylene glycol)diacrylate (PEGDA) ($M_n$=700) at 45° C.

0.100 g of PAEPBDDA was dissolved 200 µl phosphate buffer at pH 7.4 and was mixed with 0.107 g of PEGDA. The mixture was incubated at 45° C. in a water bath to form hydrogel. The gel time of the hydrogel is described in Table 4.

Example 23

Synthesis of hydrogel from poly(amino ester)s (1,4-butanediol diacrylate and 1-(2-aminoethyl)piperazine) and Poly(ethylene glycol)diacrylate (PEGDA) ($M_n$=700) at 55° C.

0.100 g of PAEPBDDA was dissolved in 200 µl phosphate buffer at pH 7.4 and was mixed with 0.107 g of PEGDA. The mixture was incubated at 55° C. in a water bath to form hydrogel. The gel time of the hydrogel is described in Table 4.

Example 24

Synthesis of hydrogel from poly(amino ester)s (Poly(ethylene glycol)diacrylate (PEGDA) ($M_n$=575) and 1-(2-aminoethyl)piperazine) and Poly(ethylene glycol)diacrylate (PEGDA) ($M_n$=700) at 35° C.

Synthesis of poly(amino ester)s from Poly(ethylene glycol)diacrylate (PEGDA) ($M_n$=575) and 1-(2-aminoethyl)piperazine 4.44 g of Poly(ethylene glycol)diacrylate (PEGDA) ($M_n$=575) in 20 ml of chloroform was added dropwise to a solution of 1.00 g of 1-(2-aminoethyl)piperazine in 15 ml of chloroform under stirring at 25° C. for a period of one hour. After completion of addition, the reaction temperature was increased to 45° C. The reaction mixture was stirred at 45° C. for 3 days. The solution was concentrated and precipitated in diethylether to obtain a water soluble poly(amino ester)s. The molecular weight of the polymer was determined by Vapour Pressure Osmometry and is summarized in Table 2.

Hydrogel Preparation 0.100 g of PAEPPEG (575) dissolved in 200 µl of phosphate buffer at pH 7.4 was mixed with 0.0497 g of PEGDA ($M_n$=700). The mixture was incubated at 35° C. in a water bath to form hydrogel. The gel time of the hydrogel is described in Table 4.

Example 25

Synthesis of Hydrogel from Piperazine Modified Polysuccinimide (PSIPIP) and Poly(Ethylene Glycol)Diacrylate (PEGDA) ($M_n$=1610) at 45° C.

0.050 g of PSIPIP dissolved in 100 µl phosphate buffer at pH 7.4 was mixed with 0.2197 g of PEGDA (Mn=1610) dissolved in 200 µl phosphate buffer at pH 7.4. The mixture was incubated at 45° C. in a water bath to form hydrogel. The gel time of the hydrogel is described in Table 4.

Example 26

Synthesis of Hydrogel from Piperazine Modified Polysuccinimide (PSIPIP) and Poly(Ethylene Glycol)Diacrylate (PEGDA) ($M_n$=2110) at 45° C.

0.050 g of PSIPIP dissolved in 100 µl phosphate buffer at pH 7.4 was mixed with 0.2880 g of PEGDA (Mn=2110) dissolved in 200 µl phosphate buffer at pH 7.4. The mixture was incubated at 45° C. in a water bath to form hydrogel. The gel time of the hydrogel is described in Table 4.

Example 27

Synthesis of Hydrogel from Amine Modified Poly(Ethylene Glycol)Diacrylate and Polyethylene Glycol)Diacrylate (PEGDA) at 25° C.

Amine Modified Poly(Ethylene Glycol)Diacrylate (PEGDADA258)

End modified poly(ethylene glycol)diacrylate ($M_n$=258) was synthesized by reacting PEGDA with excess of ethyl enediamine. The detailed synthesis was as follows, 5 g of PEGDA in 10 ml dichloromethane was added to a solution of 23 ml ethylenediamine in 10 ml dichloromethane with stirring. After complete addition the mixture was stirred for 12 hrs at 25° C. The solution was poured into a mixture of diethylether/ethanol (90/10) to obtain viscous amine capped PEGDA (PEGDADA258). The macromer was stored at 5° C.

Hydrogel Preparation 0.01799 g of amine modified polyethylene glycol diacrylate (PEGDADA258) dissolved in 100 µl of phosphate buffer at pH 7.4 was mixed with 0.100 g of PEGDA ($M_n$=700). The mixture was incubated at 25° C. in a water bath to form hydrogel. The gel time of the hydrogel is described in Table 4.

Example 28

Synthesis of Hydrogel from Amine Modified Poly(Ethylene Glycol)Diacrylate and Poly(Ethylene Glycol)Diacrylate (PEGDA) at 25° C.

Amine Modified Poly(Ethylene Glycol)Diacrylate (PEGDADA575)

End modified Poly(ethylene glycol)diacrylate ($M_n$=575) was synthesized by reacting PEGDA with excess of ethylenediamine. The detailed synthesis was as follows, 5 g of PEGDA in 10 ml dichloromethane was added to a solution of 10 ml ethylenediamine in 10 ml dichloromethane with stirring. After complete addition the mixture was stirred for 12 hrs at 25° C. The solution was poured into a mixture of diethylether/ethanol (90/10) to obtain viscous amine capped PEGDA (PEGDADA575). The macromer was stored at 5° C.

Hydrogel Preparation 0.03308 g of amine modified polyethylene glycol diacrylate (PEGDADA575) dissolved in 100 µl of phosphate buffer at pH 7.4 was mixed with 0.100 g of PEGDA ($M_n$=700). The mixture was incubated at 25° C. in a water bath to form hydrogel. The gel time of the hydrogel is described in Table 4.

Example 29

Synthesis of Hydrogel from Amine Modified Poly(Ethylene Glycol)Diacrylate and Polyethylene Glycol)Diacrylate (PEGDA) at 25° C.

Amine Modified Poly(Ethylene Glycol)Diacrylate (PEGDADA2110)

End modified poly(ethylene glycol)diacrylate ($M_n$=2110) was synthesized by reacting PEGDA with excess of ethylenediamine. The detailed synthesis was as follows, 1 g of PEGDA in 3 ml dichloromethane was added to a solution of 1 ml ethylenediamine in 10 ml dichloromethane with stirring. After complete addition the mixture was stirred for 12 hrs at 25° C. The solution was poured into a mixture of diethylether/ethanol (90/10) to obtain amine capped PEGDA (PEGDADA2110). The macromer was stored at 5° C.

Hydrogel Preparation 0.1061 g of amine modified polyethylene glycol diacrylate (PEGDADA2110) dissolved in 200 µl of phosphate buffer at pH 7.4 was mixed with 0.100 g of PEGDA ($M_n$=700). The mixture was incubated at 25° C. in a water bath to form hydrogel. The gel time of the hydrogel is described in Table 4.

Example 30

Synthesis of Hydrogel from Hexamethylenediamine Modified Polysuccinimide (PSIHD) and Acrylate (28%) Derivative of Poly(Hydroxyethyl Aspartamide) (PHEAAC) at 50° C.

Acrylate (28%) derivative of poly(hydroxyethyl aspartamide) was prepared by reacting PHEA4 with acryloyl chloride in the presence of triethylamine using a similar procedure as reported in example 12.

Hydrogel Preparation 0.01325 g of PSIHD dissolved in 100 µl of phosphate buffer at pH 7.4 was mixed with 0.050 g of PHEAAC (28%) in 100 µl of phosphate buffer at pH 7.4. The mixture was incubated at 50° C. in a water bath to form hydrogel. The gel time of the hydrogel is described in Table 4.

Example 31

Synthesis of Hydrogel from Piperazine Modified Polysuccinimide (PSIPIP) and Acrylate (11%) Derivative of Poly(Hydroxy Ethyl Aspartamide) (PHEAAC) at 40° C.

Acrylate (11%) derivative of poly(hydroxy ethyl aspartamide) was prepared by reacting PHEA1 with acryloyl chloride in the presence of triethylamine using a similar procedure as reported in example 12.

Hydrogel Preparation 0.0097 g of PS1P1P dissolved in 100 µl of phosphate buffer at pH 7.4 was mixed with 0.050 g of PHEAAC (11%) in 150 µl of phosphate buffer at pH 7.4. The mixture was incubated at 40° C. in a water bath to form hydrogel. The gel time of the hydrogel is described in Table 4.

Example 32

Synthesis of hydrogel from O,O'-Bis-(2-aminopropyl)polypropylene glycol-block-polyethylene glycol-block-polypropylene glycol (Mn=1900) and acrylate (53%) derivative of poly(hydroxyethyl aspartamide) (PHEAAC) at 50° C.

Acrylate (53%) derivative of poly(hydroxy ethyl aspartamide) was prepared by reacting PHEA5 with acryloyl chloride in the presence of triethylamine using a similar procedure as reported in example 12.

Hydrogel Preparation 0.1995 g of O,O'-Bis-(2-aminopropyl)polypropylene glycol-block-polyethylene glycol-block-polypropylene glycol (Mn=1900) dissolved in 150 µl phosphate buffer at pH 7.4 was mixed with 0.050 g of PHEAAC (53%) in 100 µl phosphate buffer at pH 7.4. The mixture was incubated at 50° C. in a water bath to form hydrogel. The gel time of the hydrogel is described in Table 4.

Example 33

Preparation of film from poly(amino ester)s (1,4-butanediol diacrylate and 1-(2-aminoethyl)piperazine) and Poly(ethylene glycol)diacrylate (PEGDA) ($M_n=700$)

0.100 g of PAEPBDDA was dissolved 200 μl phosphate buffer at pH 7.4 and was mixed with 0.107 g of PEGDA. The mixture was poured onto the flat surface maintained at 45° C. to form hydrogel film. The hydrogel was freeze dried for 48 hrs to obtain dried film. The gel time, thickness and degradation time of the dried film is described in Table 5.

Example 34

Preparation of Film from Hexamethylenediamine Modified Polysuccinimide (PSIHD) and Polyethylene Glycol)Diacrylate (PEGDA) ($M_n=700$)

0.100 g of PSIHD dissolved in 400 μl of phosphate buffer at pH 7.4 was mixed with 0.3283 g of PEGDA. The mixture was poured onto the flat surface maintained at 37° C. to form hydrogel film. The hydrogel was vacuum dried for 48 hrs to obtain dried film. The gel time, thickness and degradation time of the dried film are described in Table 5.

Example 35

Preparation of Hydrogel by Coating Poly(Ethylene Glycol)Diacrylate (PEGDA) ($M_n=700$) onto Piperazine Modified Polysuccinimide (PSIPIP)

0.100 g of PSIPIP dissolved in 400 μl of phosphate buffer at pH 7.4 was coated onto a glass substrate maintained at 37° C. To the above aqueous coating 0.191 1 g of PEGDA was coated and allowed to gel at 37° C. The gel time, thickness and degradation time of the hydrogel are described in Table 5.

Example 36

Preparation of Crosslinked Microspheres from Hexamethylenediamine Modified Polysuccinimide (PSIHD) and Polyethylene Glycol)Diacrylate (PEGDA) ($M_n=700$)

0.050 g of PSIHD dissolved in 200 μl of phosphate buffer at pH 7.4 was mixed with 0.1641 g of PEGDA. Separately, a mixture of 15 ml toluene and 15 mg sorbitan monooleate was cooled at 5° C. in a jacketed kettle equipped with mechanical stirrer and condenser. The aqueous solution was dispersed in toluene phase stirring at 1100 rpm using a syringe. This solution was maintained at 5° C. for 10 minutes. The temperature of the solution was raised to 40° C. and stirred for another 45 minutes. The formed crosslinked microspheres were washed with tetrahydrofuran and filtered. The particles formed were dried under vacuum for 24 hrs. The size of the particles was in the range 10-200 μm as observed using a polarized optical microscope.

Example 37

Preparation of Hydrogel from a Dispersion of Piperazine Modified Polysuccinimide (PSIPIP) in a Solution of Polyethylene Glycol)Diacrylate (PEGDA) ($M_n=700$) in N-Methylpyrrolidone 0.050 g of PSIPIP was dispersed in a solution of 0.095 g of PEGDA in 200 μl of N-methylpyrrolidone. The dispersion was added to 400 μl of phosphate buffer at pH 7.4. The mixture was incubated at 37° C. in a water bath to form hydrogel. The solution formed gel in 30 seconds.

Example 38

Preparation of Hydrogel from a Dispersion of Piperazine Modified Polysuccinimide (PSIPIP) and Acrylate (53%) Derivative of Poly(hydroxyethyl Aspartamide) (PHEAAC) in N-Methylpyrrolidone 0.038 g of PSIPIP and 0.050 g of PHEAAC was dispersed in 200 μl of N-methylpyrrolidone. The dispersion was added to 400 μl of phosphate buffer at pH 7.4. The mixture was incubated at 37° C. in a water bath to form hydrogel. The solution formed gel in 15 seconds.

TABLE 1

Characterization of Poly(β-aminoester) Hydrogels

| S. No | Component A | Component B | Gel time (minutes) | Water content (%) | Degradation time (hrs) |
|---|---|---|---|---|---|
| 1 | PEGDA(Mn = 700) | PEGDADA | 3 | — | 1.5 |
| 2 | PEGDA(Mn = 258) | PEGDADA | 2 | — | 2 |
| 3 | PEGDA(Mn = 700) | PAEPBDDA | 4 | 66 | 12 |
| 4 | PEGDA(Mn = 258) | PAEPBDDA | 1 | 40 | 7 |
| 5 | PEGDA(Mn = 700) | PAEPPEG | 10 | — | 2.5 |
| 6 | PEGDA(Mn = 700) | PSIED | 1.5 | 68 | 58 |
| 7 | PEGDA(Mn = 700) | PSIPD | 1 | 70 | 64 |
| 8 | PEGDA(Mn = 700) | PSIHD | 1 | 78 | 72 |
| 9 | PEGDA(Mn = 700, 0.20 mole %) | PSIHD | 2 | 65 | 5 |
| 10 | PEGDA(Mn = 700) | PSIPIP | 0.166 | 75 | 60 |
| 11 | PEGDA(Mn = 700, 0.20 mole %) | PSIPIP | 0.166 | 60 | 10 |
| 12 | PHEAAC(5% acrylate) | PSIPIP | 1 | 78 | 35 |
| 13 | PHEAAC(52% acrylate) | PSIPIP | 0.166 | 79 | 15 days |
| 14 | PHEAAC(5% acrylate) | PSIHD | 1 | 75 | 45 |
| 15 | PHEAAC(52% acrylate) | PSIHD | 1 | 82 | 52 days |
| 16 | PHEAAC(52% acrylate) | BAPPGPEGPPG (Mn = 800) | 1 | 80 | 30 |
| 17 | PHEAAC(52% acrylate) | BAPPGPEGPPG (Mn = 1900) | 1 | 64 | 52 |
| 18 | PEGDA(Mn = 700) | Lysine | 45 | 61 | >three months |
| 19 | PEGDA(Mn = 575) | Lysine | 25 | 51 | >three months |
| 20 | PHEAAC (52% acrylate) | Lysine | 1 | 86 | 35 |

POLYMER ABBREVIATIONS
PEGDA—Poly(ethylene glycol) diacrylate
PHEAAC—Acrylate derivative of poly (hydroxyethyl aspartamide)
PEGDADA—Poly(ethylene glycol) diacrylate modified with ethylenediamine
PSIED—Poly(succinimide) modified with ethylenediamine
PSIPD—Poly(succinimide) modified with 1,3-diaminopropane
PSIHD—Poly(succinimide) modified with hexamethylenediamine
PSIPIP—Poly(succinimide) modified with piperazine
PAEPPEG—Poly(amino ester)s (Poly(ethylene glycol) diacrylate (PEGDA)(Mn 258) and 1-(2-aminoethyl)piperazine)
PAEPBDDA—Poly(amino ester)s (1,4-butanediol diacrylate and 1-(2-aminoethyl)piperazine)
BAPPGPEGPPG—O,O'-Bis-(2-aminopropyl) polypropylene glycol-block-polyethylene glycol- block-polypropylene glycol

TABLE 2

Molecular weight of poly(amino ester)s

| Sl. No | Polymer abbreviation | Molecular weight ($M_n$) by Vapour Pressure Osmometry (VPO) |
|---|---|---|
| 1 | PAEPBDDA | 6,500 |
| 2 | PAEPPEG (PEG 258) | 7,100 |
| 3 | PAEPPEG (PEG 575) | 9,100 |

TABLE 3

Molecular weight of polymers using aqueous gel permeation chromatography

| Sl. No | Polymer abbreviation | $M_n$ | $M_w$ | Polydispersity index (PDI) |
|---|---|---|---|---|
| 1 | PHEA1 | 3532 | 5407 | 1.53 |
| 2 | PHEA2 | 4756 | 7846 | 1.65 |
| 3 | PHEA3 | 5727 | 8058 | 1.41 |
| 4 | PHEA4 | 8902 | 14826 | 1.66 |
| 5 | PHEA5 | 10014 | 20332 | 2.03 |
| 6 | PSIPIP | 2056 | 2709 | 1.31 |

TABLE 4

Gel time of hydrogels at various temperatures

| Sl. No | Component A | Component B | Temperature (° C.) | Gel time (minutes) |
|---|---|---|---|---|
| 1 | PEGDA($M_n$ = 700) | PAEPBDDA | 25 | 6 |
| 2 | PEGDA($M_n$ = 700) | PAEPBDDA | 45 | 2.5 |
| 3 | PEGDA($M_n$ = 700) | PAEPBDDA | 55 | 1.25 |
| 4 | PEGDA($M_n$ = 700) | PAEPPEG(575) | 35 | 25 |
| 5 | PEGDA($M_n$ = 1610) | PSIPIP | 45 | 0.25 |
| 6 | PEGDA($M_n$ = 2110) | PSIPIP | 45 | 0.33 |
| 7 | PEGDA($M_n$ = 700) | PEGDADA258 | 25 | 2 |
| 8 | PEGDA($M_n$ = 700) | PEGDADA575 | 25 | 2.5 |
| 9 | PEGDA($M_n$ = 700) | PEGDADA2110 | 25 | 30 |
| 10 | PHEAAC (11%) | PSIPIP | 40 | 0.5 |
| 11 | PHEAAC (53%) | BAPPGPEGPPG (Mn = 1900) | 50 | 0.5 |
| 12 | PHEAAC (28%) | PSIHD | 50 | 3 |

TABLE 5

Characterization of hydrogel films and coating

| Sl. No | Component A | Component B | Gel time (minutes) | Thickness (mm) | Degradation time (hrs) |
|---|---|---|---|---|---|
| 1 | PEGDA(Mn = 700) | PAEPBDDDA | 2.5 | 0.300 | 4 |
| 2 | PEGDA(Mn = 700) | PSIHD | 1 | 0.160 | 4 |
| 3 | PEGDA(Mn = 700) | PSIPIP | 0.5 | 0.450 | 30 |

Accordingly, the present invention provides a fast curing β-amino ester based biodegradable polymeric hydrogel. The invention focuses on eliminating the earlier limitations of crosslinked β-amino ester systems such as the use of use of photoirradiation, presence of residual initiators, organic solvents, other reagents and high reaction temperature. Also the rate of formation of hydrogels is much faster than that of β-amino ester based crosslinked systems reported earlier. These advantages of fast curing biodegradable hydrogel reported herein will find applications in controlled drug delivery, cell release and tissue engineering.

What is claimed is:

1. A biodegradable polymeric hydrogel composition comprising a water-soluble poly(hydroxyethyl aspartamide) (PHEAAC) having an acrylate group polymerized with a water soluble poly(succinimide) having an amine group to form a β-aminoester linkage between the acrylate group of the PHEAAC and the amine group of the poly(succinimide);
   wherein the poly(hydroxyethyl aspartamide) (PHEAAC) has a molecular weight in the range of 5,000 to 22,000 Da and has an acrylate modification of between 5 mole % and 53 mole %; and
   wherein the amine group is selected from the group consisting of primary and secondary amine.

2. The biodegradable hydrogel composition as claimed in claim 1, wherein the primary amine is selected from the group consisting of ethylenediamine, 1,3-diaminopropane, and hexamethylenediamine.

3. The biodegradable hydrogel composition as claimed in claim 1, wherein the secondary amine is piperazine.

4. The biodegradable polymeric hydrogel composition as claimed in claim 1 wherein the β-aminoester linkage is formed at temperatures of between 25° C. to 55° C.

5. A process for the synthesis of a biodegradable hydrogel, wherein the process comprises:
   reacting a water-soluble poly(hydroxyethyl aspartamide) (PHEAAC) having an acrylate group with a water soluble poly(succinimide) having an amine group to form a β-aminoester linkage between the acrylate group of the PHEAAC and the amine group of the poly(succinimide);
   wherein the poly(hydroxyethyl aspartamide) (PHEAAC) has a molecular weight in the range of 5,000 to 22,000 Da and has an acrylate modification of between 5 mole % and 53 mole %;
   wherein the amine group is selected from the group consisting of primary and secondary amine;
   in an aqueous medium in the temperature range of 25-55° C. until a hydrogel is formed.

6. The process claimed in claim 5, wherein formation of a hydrogel is achieved in a time period of between 10 seconds to 5 hours.

7. The process claimed in claim 6, wherein formation of a hydrogel is achieved in the time period of between 10 seconds to 45 minutes.

8. The biodegradable hydrogel as claimed in claim 1, wherein the degradation time of the hydrogel is in the range of 1.5 hour to 55 days.

9. The process as claimed in claim 5, wherein the reaction is carried out at temperature in the range 30 to 40° C.

10. The process as claimed in claim 5, wherein the hydrogel is dried by tray drying, vacuum drying or freeze drying.

11. The process as claimed in claim 5, wherein the PHEAAC and the poly(succinimide) are mixed with each other and dispersed in a non-aqueous medium prior to reacting them to form the hydrogel.

12. The process as claimed in claim 5, wherein the PHEAAC and the poly(succinimide) in an aqueous medium is cast into a film which is formed into a hydrogel by heating the film to a temperature of 55° C.

13. The process as claimed in claim 5, wherein an aqueous solution of PHEAAC is coated on a substrate, and an aqueous solution of poly(succinimide) is applied to the PHEAAC, and a hydrogel is formed by heating the film to a temperature of 55° C.

14. A biodegradable polymeric hydrogel composition, consisting of a water soluble polymer having an acrylate group polymerized through a β-aminoester linkage with a water soluble polymer having an amine group;

wherein the water soluble polymer having an acrylate group is selected from the group consisting of poly(ethylene glycol)diacrylate (PEGDA) having a molecular weight of 200 to 2500 Da and acrylate derivative of poly(hydroxyethyl aspartamide) (PHEAAC) having a molecular weight of 5,000 to 22,000 Da and has an acrylate modification of between 5 mole % and 53 mole %; and wherein the water soluble polymer having an amine group is selected from the group consisting of amine terminated poly(ethylene glycol), poly(succinimide) containing an amine functionality, poly(amino ester) containing an amine functionality, and an amino acid.

15. The biodegradable hydrogel composition as claimed in claim 14, wherein the amine functionality of the water soluble polymer having an amine group is a primary amine or a secondary amine.

16. The biodegradable hydrogel composition as claimed in claim 14, wherein the degradation time of the hydrogel is in the range of 1.5 hours to 55 days.

17. The biodegradable hydrogel composition as claimed in claim 14, wherein the β-aminoester linkage is formed at temperatures of between 25° C. to 55° C.

18. A process for the synthesis of a biodegradable hydrogel, wherein the process comprises:
reacting a water soluble polymer having an acrylate group selected from the group consisting of poly(ethylene glycol)diacrylate (PEGDA) having a molecular weight of 200 to 2500 Da and acrylate derivative of poly(hydroxyethyl aspartamide) (PHEAAC) having a molecular weight of 5,000 to 22,000 Da and has an acrylate modification of between 5 mole % and 53 mole %;
with a water soluble polymer having an amine group selected from the group consisting of amine terminated poly(ethylene glycol), poly(succinimide) containing an amine functionality, poly(amino ester) containing an amine functionality, and an amino acid;
in an aqueous medium in the temperature range of 25-55° C. until a hydrogel is formed.

19. The process as claimed in claim 18, wherein the reaction is carried out at temperature in the range 30 to 40° C.

* * * * *